United States Patent
Grass et al.

(10) Patent No.: US 7,505,551 B2
(45) Date of Patent: Mar. 17, 2009

(54) METHOD AND DEVICE FOR FLOW RECONSTRUCTION

(75) Inventors: Michael Grass, Buchholz in der Nordheide (DE); Volker Rasche, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 435 days.

(21) Appl. No.: 10/568,838

(22) PCT Filed: Aug. 10, 2004

(86) PCT No.: PCT/IB2004/051432

§ 371 (c)(1),
(2), (4) Date: Feb. 17, 2006

(87) PCT Pub. No.: WO2005/018457

PCT Pub. Date: Mar. 8, 2005

(65) Prior Publication Data

US 2006/0210134 A1    Sep. 21, 2006

(30) Foreign Application Priority Data

Aug. 20, 2003  (EP) .................................. 03102610

(51) Int. Cl.
*A61B 6/03*  (2006.01)

(52) U.S. Cl. .......................................... 378/8; 600/428

(58) Field of Classification Search ..................... 378/8, 378/95; 600/428
See application file for complete search history.

(56) References Cited

U.S. PATENT DOCUMENTS

| | | | |
|---|---|---|---|
| 4,577,222 A | 3/1986 | Kruger et al. | |
| 6,337,992 B1 | 1/2002 | Gelman | |
| 6,442,235 B2 | 8/2002 | Klotz et al. | |
| 6,449,337 B1 * | 9/2002 | Honda et al. | 378/117 |
| 2003/0040669 A1 | 2/2003 | Grass et al. | |

FOREIGN PATENT DOCUMENTS

JP    2001149360 A  *  6/2001

* cited by examiner

*Primary Examiner*—Chih-Cheng G Kao

(57) ABSTRACT

The invention relates to a method and a device for the three-dimensional reconstruction of the flow conditions in a vascular system (3), in which, in a first phase after the beginning of a contrast-medium injection, X-ray projection pictures are produced from the same direction (A) at a high picture-taking rate in order to observe the inflow of the contrast medium. When the contrast medium fills the vascular system (3), a rotation of the Xray device (1) takes place during which projection pictures are produced at a lower picture taking rate and/or at a lower radiation dose, from which pictures the three-dimensional structure of the vascular tree can be reconstructed. Optionally, at the end of the rotation, projection pictures may again be taken from a fixed direction that observe the drainage of the contrast medium from the vascular system (3).

20 Claims, 1 Drawing Sheet

METHOD AND DEVICE FOR FLOW RECONSTRUCTION

The invention relates to a method and a device for the three-dimensional reconstruction of the flow conditions in a vascular system with the aid of two-dimensional projections of the vascular system during a contrast-medium injection.

To assess diseases of the vascular system, it is desirable to know the flow conditions prevailing therein in conjunction with a three-dimensional model of the vascular tree. In this connection, it is known, for example, from U.S. Pat. No. 4,577,222 to inject contrast mediums into a vascular system and to track the spreading of the contrast medium with the aid of a series of projection pictures. Furthermore, it is known from three-dimensional X-ray rotation angiography ("3D-RA") to reconstruct a three-dimensional vascular tree from two-dimensional projection pictures of the vascular tree taken from different directions. In the production of such angiograms, a contrast medium is also as a rule injected so that the vascular tree to be recorded is displayed as well as possible on the X-ray pictures.

Against this background, it was the object of the present invention to provide means for the three-dimensional reconstruction of the flow conditions in a vascular system, which means entail as little exposure as possible for the patient.

This object is achieved by a device and method having the features as described herein. Advantageous refinements are also described herein.

The device according to the invention serves for the three-dimensional reconstruction of the flow conditions in a vascular system with the aid of two-dimensional projections of the vascular system during a contrast-medium injection. "Contrast medium" is to be understood in this regard in a wide sense as meaning any medium or object whose movement in a vascular system is observable and during this process makes possible conclusions relating to the flow conditions in the vascular system. The device comprises the following components:

An imaging device for producing two-dimensional projection pictures of the vascular system taken from different directions. Said device may be, in particular, a rotation X-ray unit, such as is known, for example, from computer tomography.

An injection device for the controlled injection of a contrast medium into the vascular system. As a rule, such an injection device will comprise an injection pump and a catheter, the catheter being pushed forward via an access to the vascular system up to an examination point of interest (for example, the heart).

A control unit that is coupled to the imaging device and that is designed to drive the imaging device in accordance with the following steps:

a) First step: production of projection pictures of the vascular system taken from the same projection direction during the inflow of the contrast medium, that is to say from the beginning of a contrast-medium injection. The chosen picture-taking rate is to be high in this case so that the spreading of the contrast medium in the vascular system is recorded with good time resolution in the projection pictures.

b) Second step: Rotation of the imaging device around the vascular system to produce projection pictures taken from different directions while the contrast medium injected in the first step fills the vascular system. The projection pictures produced in this way show the entire vascular system in an optimum way so that the three-dimensional vascular tree can be reconstructed from said pictures. The methods known from rotation angiography, which, inter alia, may comprise a selection of projection pictures from the same ECG or heartbeat phase may, in particular, be used for the reconstruction.

The device described makes it possible to record both the spreading of the contrast medium and consequently the flow conditions with a single contrast-medium injection, as well as to reconstruct the vascular tree three-dimensionally. The stressing of the patient by the contrast medium is consequently kept to a minimum level.

In particular, if the imaging device is an X-ray unit, the control unit is furthermore optionally designed to effect production of projection pictures at a lower picture-taking rate and/or at a lower radiation dose during the rotation of the imaging device. The lower radiation dose can be brought about in the case of an X-ray unit, for example, by a suitable adjustment of the tube current and/or the tube voltage. Reducing the picture-taking rate and/or the radiation dose ensures that the radiation exposure of the patient is limited to a minimum while the rotation pictures are taken.

In accordance with a further aspect of the device, the control unit is furthermore designed to drive the imaging device after completion of the rotation in such a way that it produces further projection pictures taken from a constant projection direction. Preferably, this production takes place again at a high picture-taking rate. Such pictures at the end of the rotation make it possible also to observe the draining of the contrast medium from the vascular system in a time-resolved manner.

In accordance with another aspect of the device, the control unit is designed to initiate the beginning of the rotation of the imaging device as a function of an image analysis of the projection pictures taken during the inflow of the contrast medium. In particular, it is possible to determine from the projection pictures produced during the inflow the instant in time at which the contrast medium fills the entire vascular tree, i.e. the inflow process is complete and the conditions exist for the rotation pictures.

Furthermore, the control unit may also be coupled to the injection device for the contrast medium in order to record and/or to control the injection process automatically. During a recording of the injection process, the control unit can, for example, obtain information about when a user initiates a contrast-medium injection so that the control unit can effect the production of projection pictures in harmony therewith. If the control unit can control the injection device, it can initiate the injection operation automatically itself.

The invention furthermore relates to a method for the three-dimensional reconstruction of the flow conditions in a vascular system with the aid of two-dimensional projection pictures of the vascular system taken during a contrast-medium injection that comprises the following steps:

a) Production of projection pictures taken from the same projection direction with a high picture-taking rate during the inflow of the contrast medium;

b) Production of projection pictures of the vascular system taken from different directions while the vascular system is being filled with contrast medium.

The method implements, in general form, the steps that can be executed with a device of the above-described type. For the explanation of details, advantages and variants of the method, reference is therefore made to the above description.

In particular, the projection pictures can be produced in the method with the aid of X-rays. In order to limit the radiation exposure for the patient to a minimum during this process, the picture-taking rate and/or the radiation dose is reduced to a necessary level during step b) compared with the conditions in step a).

Furthermore, projection pictures are preferably produced again from a fixed direction after the termination of step b) while the contrast medium is draining from the vascular system. As a result of tracking the contrast-medium drainage, a second observation is available that permits an assessment of the flow conditions in the vascular system.

These and other aspects of the invention are apparent from and will be elucidated with reference to the embodiments described hereinafter.

IN THE DRAWINGS

Figure 3:
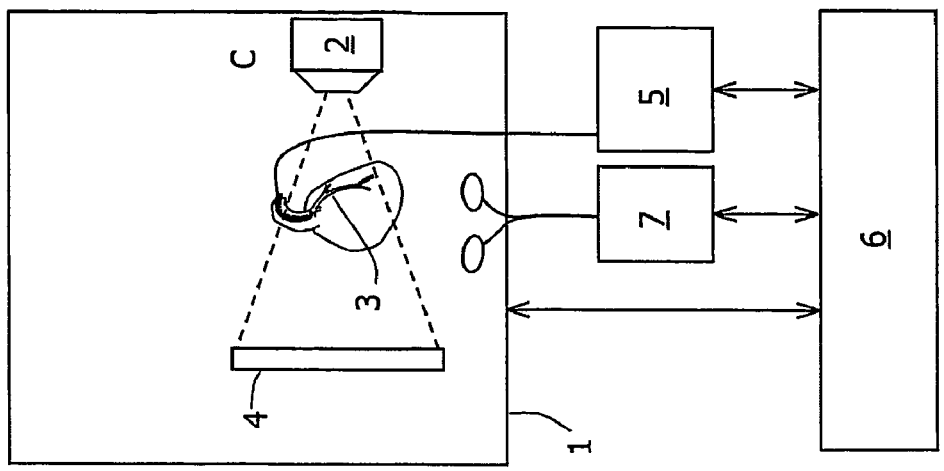
FIG. 3 shows the device of FIG. 1 during the drainage of the contrast medium.

The system shown in the Figures is based on a medical application, but the present invention is not limited thereto. Within the framework of the medical application, the flow conditions are to be observed and reconstructed three-dimensionally in a vascular system 3, for example, in the coronary vessels. For this purpose, the device comprises a rotation X-ray unit 1 having an X-ray source 2 and an X-ray detector 4 for producing two-dimensional projections of the vascular system 3 and also an injection device 5 for injecting a contrast medium into the vascular system. The injection device 5 may comprise, in particular, a pump and also a catheter leading into the vascular system. Furthermore, the device is coupled to a control unit 6 (for example, a workstation) that can control the X-ray unit 1 and evaluate pictures produced therefrom. Finally, the system also comprises an ECG unit 7 that is coupled to the control unit 6 in order to make possible a correlation of the picture-taking procedure with the heartbeat phase.

The device described makes it possible to record from a single contrast-medium injection or with a single contrast-medium bolus both the flow conditions with time and to reconstruct the vascular system spatially. In order to achieve this, the control unit 6 is equipped with a suitable program for activating the device 1 so that the picture-taking procedure described in detail below can be executed.

Figure 1:
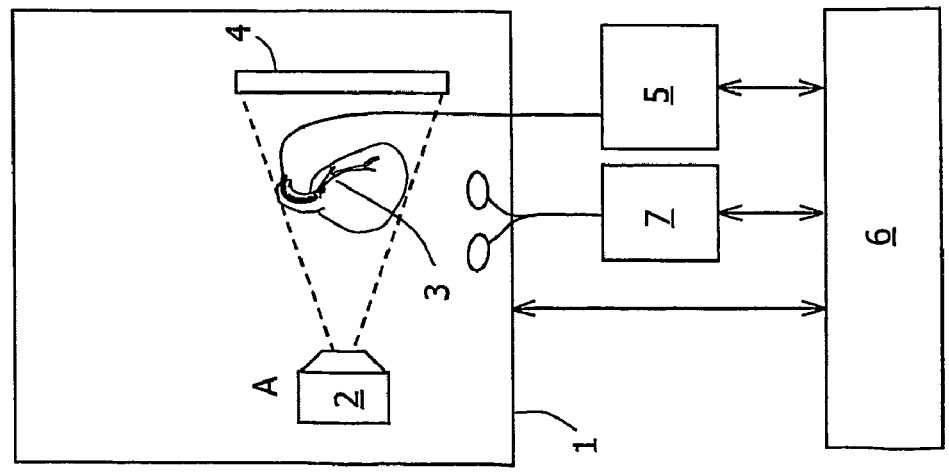
FIG. 1 shows diagrammatically the device according to the invention for the three-dimensional reconstruction of the flow conditions in a vascular system during the inflow of the contrast medium.

In the first step shown in FIG. 1 of the picture-taking procedure, projection pictures of the vascular system 3 are produced from a constant projection direction A at a high picture-taking rate of typically 30-80 pictures per second, preferably approximately 50 pictures per second. In this connection, at the beginning of the picture-taking series, the contrast-medium injection is effected so that the inflow of the contrast medium into the vascular system can be reflected in a time-resolved manner in the pictures.

When the contrast medium fills the entire vascular system 3, the second phase of the picture-taking procedure can be initiated manually by a user or automatically by the control unit 6 with a rotation of the X-ray device 2, 4 around the vascular system 3. An automatic initiation may take place, for example, by an image analysis of the projection pictures produced from position A. Equally, the control unit 6 can determine by a coupling to the injection device 5 when a certain amount of contrast medium has been injected or a certain time has elapsed since the beginning of the injection in order then to initiate the rotation. During the rotation of the X-ray device, projection pictures are produced from different directions $B_i$ from which the three-dimensional shape of the vascular tree can be reconstructed using known methods.

Figure 2:
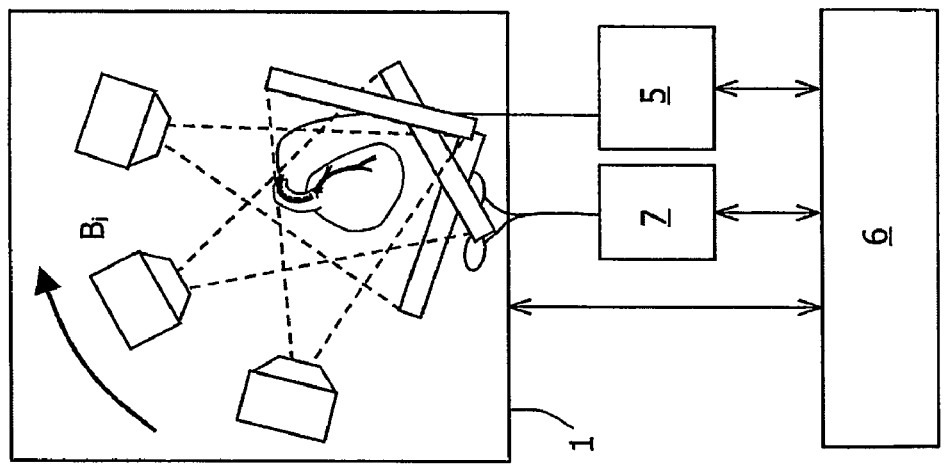
FIG. 2 shows the device of FIG. 1 during the rotation of the X-ray device.

FIG. 3 shows an optional last step in which, after termination of the rotation (FIG. 2), X-ray projections of the vascular system 3 are once again produced from a fixed projection direction C. In these pictures, the drainage of the contrast medium from the vascular system in a time-resolved manner can, in particular, be observed so that further items of information are available for the flow reconstruction. In addition, this observation also makes it possible to calculate from additional parameters such as, for example, the times for which the contrast medium remains in a portion of the vascular system.

The initial and the final positions of the rotation of the X-ray system must of course be suitably calibrated. Furthermore, it is possible to dispense with the stationary picture-taking phase in accordance with FIG. 1 if suitable pictures for the time assessment of the flow are produced at the end of the injection (FIG. 3).

The invention claim is:

1. A device for the three-dimensional reconstruction of flow conditions in a vascular system using two-dimensional projections of the vascular system during a contrast-medium injection, comprising;
    an imaging device for producing two-dimensional projection pictures of the vascular system taken from different directions;
    an injection device for controlled injection of a contrast medium into the vascular system;
    a control unit that is coupled to the imaging device and that is designed to drive the imaging device in accordance with the following steps:
        a) production of projection pictures taken from the same projection direction at a high picture-taking rate during inflow of the contrast medium after a contrast-medium injection;
        b) rotation of the imaging device around the vascular system and production of projection pictures taken from different directions while the vascular system is filled with the contrast medium;
        c) production of projection pictures from a fixed direction during drainage of the contrast medium from the vascular system.

2. A device as claimed in claim 1, wherein the imaging device is a rotation X-ray unit.

3. A device as claimed in claim 2, wherein during rotation of the rotation X-ray unit, the projection pictures are produced at a lower picture-taking rate.

4. The device of claim 2, wherein the projection pictures are produced at a lower radiation dose during rotation of the rotation X-ray unit.

5. A device as claimed in claim 1, wherein the control unit is designed to drive the imaging device after completion of the rotation to produce projection pictures taken from a fixed projection direction at a higher picture-taking rate.

6. A device as claimed in claim 1, wherein the control unit is designed to initiate the beginning of the rotation as a function of an image analysis of the projection pictures produced during the inflow of the contrast medium.

7. A device as claimed in claim 1, wherein the control unit is coupled to the injection device in order to record and/or to control the injection process.

8. The device of claim 1, wherein the control unit initiates the rotation based on at least one of an amount of time since commencing the contrast medium injection and an amount of the contrast medium that has been injected.

9. The device of claim 1, wherein the reconstruction is performed using a selection of the projection pictures from at least step b) during the same heartbeat phase.

10. A method for three-dimensional reconstruction of flow conditions in a vascular system using two-dimensional projections of the vascular system during a contrast-medium injection, comprising:
   a) production of projection pictures taken from the same projection direction at a high picture-taking rate during the inflow of the contrast medium;
   b) production of projection pictures of the vascular system taken from different directions while the vascular system is filled with the contrast medium; and
   c) production of projection pictures from a fixed direction during drainage of the contrast medium from the vascular system after step b).

11. A method as claimed in claim 10, wherein the projection pictures are produced by means of X-rays.

12. The method of claim 11, wherein the radiation dose is reduced during step b).

13. A method as claimed in claim 10, wherein the picture-taking rate is reduced during step b).

14. A method as claimed in claim 10, further comprising rotating an imaging device to capture the projection pictures of step b) and commencing the rotation of the imaging device based on an image analysis of the projection pictures in step a).

15. The method of claim 10, further comprising rotating an imaging device to capture the projection pictures of step b) and commencing the rotation of the imaging device based on at least one of an amount of time since commencing the contrast medium injection and an amount of the contrast medium that has been injected.

16. The method of claim 10, further comprising performing the reconstruction using a selection of the projection pictures from at least step b) during the same heartbeat phase.

17. A method for three-dimensional reconstruction of flow conditions in a vascular system using two-dimensional projections of the vascular system during a contrast-medium injection, the method comprising capturing a first set of images of the vascular system taken from different directions while the vascular system is filled with the contrast medium; and capturing a second set of images from a fixed direction during drainage of the contrast medium from the vascular system.

18. The method of claim 17, further comprising capturing a third set of images of the vascular system taken from the same direction during inflow of the contrast medium; and performing image analysis of the third set to determine commencement of capturing the second set of images.

19. The method of claim 18, further comprising performing the reconstruction using a selection of images during the same heartbeat phase from at least the first set of images.

20. The method of claim 18, further comprising reducing radiation exposure during the capturing of the first set of images.

\* \* \* \* \*